United States Patent
Ben Oren et al.

(10) Patent No.: US 10,575,904 B1
(45) Date of Patent: Mar. 3, 2020

(54) APPARATUS AND METHOD FOR SELECTIVE SUBMUCOSAL ABLATION

(71) Applicant: Digma Medical Ltd., Petah Tikva (IL)

(72) Inventors: Ilan Ben Oren, Modiin (IL); Boaz Behar, Ganey Tikva (IL)

(73) Assignee: DIGMA MEDICAL LTD., Petah Tikva (IL)

( * ) Notice: Subject to any disclaimer, the term of this patent is extended or adjusted under 35 U.S.C. 154(b) by 0 days.

(21) Appl. No.: 15/676,141

(22) Filed: Aug. 14, 2017

Related U.S. Application Data

(60) Provisional application No. 62/374,843, filed on Aug. 14, 2016.

(51) Int. Cl.
*A61B 18/14* (2006.01)
*A61B 18/24* (2006.01)
*A61B 18/00* (2006.01)

(52) U.S. Cl.
CPC .......... *A61B 18/24* (2013.01); *A61B 18/1492* (2013.01); *A61B 2018/0022* (2013.01); *A61B 2018/00577* (2013.01)

(58) Field of Classification Search
None
See application file for complete search history.

(56) References Cited

U.S. PATENT DOCUMENTS

| | | |
|---|---|---|
| 3,858,577 A | 1/1975 | Bass et al. |
| 5,029,574 A | 7/1991 | Shimamura et al. |
| 5,693,043 A | 12/1997 | Kittrell et al. |
| 6,134,003 A | 10/2000 | Tearney et al. |
| 6,485,413 B1 | 11/2002 | Boppart et al. |
| 6,832,114 B1 | 12/2004 | Whitehurst et al. |
| 6,914,733 B2 | 7/2005 | Dong et al. |

(Continued)

FOREIGN PATENT DOCUMENTS

| | | |
|---|---|---|
| EP | 0288576 | 11/1988 |
| EP | 1567082 | 8/2005 |

(Continued)

OTHER PUBLICATIONS

Wikipedia (2012) "Submucosa" (https://en.wikipedia.org/wiki/Submucosa), retrieved Oct. 22, 2019.

(Continued)

*Primary Examiner* — William J Levicky
(74) *Attorney, Agent, or Firm* — The Roy Gross Law Firm, LLC; Roy Gross

(57) ABSTRACT

Device and method for selectively ablating a submucosal layer of a duodenal wall and/or of sensory neurons therein, including a laser transmitting element coupled with the catheter body and configured to transmit a laser beam having a spot diameter of less than 200 microns and to provide an ablative dose of 0.5-2.5 J/mm; wherein the laser beam is configured to selectively ablate an area of the submucosal layer that is at least twice the size of the spot diameter, while essentially preventing damage of the surrounding mucosal, muscularis and/or serosal layers of the duodenal wall; and an expandable member configured to stretch the duodenal wall and to generate a fixed distance between the catheter's laser transmitting element and the duodenal wall.

16 Claims, 7 Drawing Sheets
(4 of 7 Drawing Sheet(s) Filed in Color)

(56) References Cited

U.S. PATENT DOCUMENTS

| | | |
|---|---|---|
| 7,096,070 B1 | 8/2006 | Jenkins et al. |
| 7,363,076 B2 | 4/2008 | Yun et al. |
| 7,430,450 B2 | 9/2008 | Imran |
| 7,494,661 B2 | 2/2009 | Sanders |
| 7,582,081 B2 | 9/2009 | Hofer et al. |
| 7,620,455 B2 | 11/2009 | Maschino |
| 7,835,074 B2 | 11/2010 | Jacobsen et al. |
| 8,095,218 B2 | 1/2012 | Gross et al. |
| 8,150,518 B2 | 4/2012 | Levin et al. |
| 8,340,760 B2 | 12/2012 | Dobak, III |
| 8,568,399 B2 | 10/2013 | Azamian et al. |
| 2002/0019627 A1* | 2/2002 | Maguire ............ A61B 18/1492 606/27 |
| 2002/0183622 A1 | 12/2002 | Zuluaga et al. |
| 2003/0144708 A1 | 7/2003 | Starkebaum |
| 2004/0082859 A1 | 4/2004 | Schaer |
| 2004/0172088 A1 | 9/2004 | Knudson et al. |
| 2004/0210278 A1* | 10/2004 | Boll ........................ A61B 18/24 607/89 |
| 2004/0215180 A1 | 10/2004 | Starkebaum et al. |
| 2004/0248188 A1 | 12/2004 | Sanders |
| 2005/0183732 A1 | 8/2005 | Edwards |
| 2005/0251116 A1 | 11/2005 | Steinke et al. |
| 2006/0122584 A1 | 6/2006 | Bommannan et al. |
| 2007/0016262 A1 | 1/2007 | Gross et al. |
| 2007/0081236 A1 | 4/2007 | Tearney et al. |
| 2007/0179487 A1 | 8/2007 | Tearney et al. |
| 2008/0086180 A1 | 4/2008 | Ben-Ezra et al. |
| 2008/0275445 A1 | 11/2008 | Kelly et al. |
| 2009/0030473 A1 | 1/2009 | Khawaled et al. |
| 2009/0062881 A1 | 3/2009 | Gross et al. |
| 2009/0086213 A1 | 4/2009 | Masuda |
| 2009/0234417 A1 | 9/2009 | Pastena et al. |
| 2009/0253990 A1 | 10/2009 | Lieber et al. |
| 2010/0049188 A1 | 2/2010 | Nelson et al. |
| 2010/0076299 A1* | 3/2010 | Gustus ................. A61B 18/245 600/411 |
| 2010/0114150 A1 | 5/2010 | Magal |
| 2010/0268297 A1 | 10/2010 | Neisz |
| 2010/0280504 A1 | 11/2010 | Manzke et al. |
| 2011/0130708 A1 | 6/2011 | Perry et al. |
| 2011/0160622 A1* | 6/2011 | McArdle ............. A61F 9/00825 601/2 |
| 2011/0208173 A1 | 8/2011 | Sobotka et al. |
| 2011/0208175 A1 | 8/2011 | Sobotka et al. |
| 2011/0257641 A1 | 10/2011 | Hastings et al. |
| 2011/0301455 A1* | 12/2011 | Numajiri ................ A61B 3/102 600/425 |
| 2012/0179228 A1 | 7/2012 | Decharms |
| 2013/0178910 A1 | 7/2013 | Azamian et al. |
| 2013/0197555 A1 | 8/2013 | Schaer |
| 2013/0345670 A1 | 12/2013 | Rajagopalan et al. |
| 2014/0017635 A1 | 1/2014 | Fischer |
| 2014/0074077 A1 | 3/2014 | Lane |
| 2014/0088575 A1 | 3/2014 | Loeb |
| 2014/0088581 A1 | 3/2014 | Kelly et al. |
| 2014/0187619 A1 | 7/2014 | Pasricha et al. |
| 2015/0148738 A1 | 5/2015 | Caplan et al. |
| 2015/0359594 A1 | 12/2015 | Ben-Oren et al. |

FOREIGN PATENT DOCUMENTS

| | | |
|---|---|---|
| WO | 02/00172 | 1/2002 |
| WO | 2004/069331 | 8/2004 |
| WO | 2004/112883 | 12/2004 |
| WO | 2007/007339 | 1/2007 |
| WO | 2008/041233 | 4/2008 |
| WO | 2008/137757 | 11/2008 |
| WO | 2011/156736 | 12/2011 |
| WO | 2012/099974 | 7/2012 |
| WO | 2012/122460 | 9/2012 |
| WO | 2013/012892 | 1/2013 |
| WO | 2013/082587 | 6/2013 |
| WO | 2013/130655 | 9/2013 |
| WO | 2013/159066 | 10/2013 |
| WO | 2014/022436 | 2/2014 |
| WO | 2014/026055 | 2/2014 |
| WO | 2014/055997 | 4/2014 |
| WO | 2014118738 | 8/2014 |
| WO | 2014/197632 | 12/2014 |
| WO | 2015/159296 | 10/2015 |
| WO | 2015159296 | 10/2015 |

OTHER PUBLICATIONS

Cummings et al., (2004) Gastric bypass for obesity: mechanisms of weight loss and diabetes resolution. J Clin Endocrinol Metab 89(6): 2608-15.

Dougherty et al., (1998) Photodynamic therapy. J Natl Cancer Inst 90(12): 889-905.

Myslovich (2001) Stomach and duodenum ulcer: comparing the efficiency of three laser therapeutic techniques. Proc. SPIE 4422, Low-Level Laser Therapy, 74 (Apr. 26, 2001); doi:10.1117/12.425517.

Oraevsky et al., (1996) Plasma mediated ablation of biological tissues with nanosecond-to-femtosecond laser pulses: relative role of linear and nonlinear absorption. IEEE Journal of Selected Topics in Quantum Electronics 2(4): 801-809.

Pories and Albrecht (2001) Etiology of type II diabetes mellitus: role of the foregut. World J Surg 25(4): 527-31.

Rubino and Gagner (2002) Potential of surgery for curing type 2 diabetes mellitus. Ann Surg 236(5): 554-9.

Rubino et al., (2004) The early effect of the Roux-en-Y gastric bypass on hormones involved in body weight regulation and glucose metabolism. Ann Surg 240(2): 236-42.

Rubino et al., (2006) The mechanism of diabetes control after gastrointestinal bypass surgery reveals a role of the proximal small intestine in the pathophysiology of type 2 diabetes. Ann Surg 244(5): 741-9.

Verdam et al., (2012) An update on less invasive and endoscopic techniques mimicking the effect of bariatric surgery. J Obes 2012: 597871.

\* cited by examiner

APPARATUS AND METHOD FOR SELECTIVE SUBMUCOSAL ABLATION

TECHNICAL FIELD

The disclosure generally relates to an apparatus and method for optimized duodenal submucosal ablation having minimal impact on neighboring duodenal layers.

BACKGROUND

Obesity is thought to be one of the primary causes of type 2 diabetes, especially in people who are genetically predisposed for the disease. Obesity is often treated by performing a bariatric surgery procedure (also known as weight-loss surgery) on the gastrointestinal tract of an obese patient in order to reduce weight. Multiple clinical studies and reports have indicated that in addition to weight-loss, certain bariatric surgery procedures can contribute to remission or improvement in disease management of type-2 diabetes, as well as to reduction in insulin resistance. This is specifically the case in certain bariatric procedures that bypass the proximal part of the gastrointestinal (GI) tract, such as Roux-en-Y gastric bypass (RYGB), duodenal-jejunal bypass (DJB) surgery and gastrojejunal bypass (GJB) surgery, all aimed at bypassing the duodenum. Unfortunately, bariatric surgery is associated with high risk and high cost and is not the optimal solution for management of the majority of T2D and non-obese patients, estimated at hundreds of millions worldwide. Consequently, bariatric surgery is typically not considered a disease management tool for the majority of T2D patients.

Attempts to gain effects similar to bariatric surgery include the use of minimally invasive devices, such as those inserted endoluminally, including staplers for reducing stomach size, intra-gastric balloons, implantation of electrical stimulators that intervene with stomach function (gastric electrical stimulation), sleeves that bypass the duodenum (e.g. EndoBarrier®, GI Dynamics™ and radio-frequency (RF) ablation applied to the surface of the organ with non-penetrating electrodes, which target duodenum mucosa, or by ablation of the area around the pyloric sphincter. However, these methods suffer from certain inherent limitations, such association with adverse events and unwarranted side effects (e.g. vomiting, nausea, abdominal pain, mucosal tear, bleeding, migration and obstruction), necessitating early device removal, complications, limited or even lack of efficacy.

Laser ablation has been suggested as a method for selectively blocking part of the neural activity in the small intestine, and preferably in the duodenum of a subject. However, generation of neural impairment within the wall of the intestine is challenging, because the wall is very thin, and inter as well as intra subject variability in wall thickness high. In addition, due to its many folds and sensitive secretion elements, uncontrolled ablation may cause severe injury and even perforation of the wall. In addition, injury of nerve cells, axons, etc. may lead to healing and recovery if not strong enough and prevent from providing a sustainable effect. As ganglion cells are spread throughout the duodenum wall, it is beneficial to induce a significant effect in large areas of the wall.

Accordingly, it would be advantageous to be able to provide ablation in a controlled manner that optimizes selective yet wide ablation within the submucosal layer while causing minimal collateral damage.

SUMMARY OF THE INVENTION

The present disclosure relates to methods, devices and systems for efficiently ablating the submucosal layer of the duodenum essentially without causing significant damage to the mucosal, muscularis and/or serosal layers of the duodenal wall.

Surprisingly, the inventors of the present invention found that providing a relatively large dose of ablative energy while utilizing a laser generating a spot diameter of less than 100 microns caused a wider lateral impact to the target layer, namely the submucosal layer, while only minimally effecting the surrounding mucosal, muscularis and/or serosal layers of the duodenal wall. In fact, the lateral impact caused to the submucosal layer was surprisingly superior to the impact obtained using lasers generating a larger spot diameter. This advantageously increases the changes that the ablation of the neural structures (nerve cells as ganglions, plexuses, axon, etc.) will be sustainable and ensures that far less points of impact are required to bring about the desired changes to the submucosal layers, thus shortening the duration of the ablation procedure. In addition, it was advantageously found that a relatively large ablative dose may be provided, without jeopardizing safety, i.e. without causing significant damage to the surrounding layers.

Advantageously, it was further found that stretching the duodenal wall, using an expandable member provides an essentially constant distance between the point of laser emission and the duodenal wall during the entire procedure, such that the circumferential ablation will be of an essentially same dose of laser energy, regardless of its position and/or orientation.

According to some embodiments, there is provided a method for selectively ablating a submucosal layer of a duodenal wall and/or of sensory neurons therein, the method including: inserting a catheter into a duodenum of a subject; deploying an expandable member delivered by the catheter, thereby stretching the duodenal wall and generating a fixed distance between the catheter's laser transmitting element and the duodenal wall; transmitting a laser beam in a direction essentially perpendicular to a longitudinal axis of the catheter, towards the duodenal wall, wherein the laser beam has a spot diameter of less than 200 microns and is configured to provide an ablative dose of 0.5-2.5 J/mm; and wherein the laser beam is configured to selectively ablate an area of the submucosal layer that is at least twice the size of the spot diameter, while essentially preventing damage of the surrounding mucosal, muscularis and/or serosal layers of the duodenal wall.

According to some embodiments, the laser beam has a wavelength of 1550 or 1567 nm.

According to some embodiments, the laser beam has a spot diameter of 100 microns or less.

According to some embodiments, the laser beam is configured to selectively ablate an area of the submucosal layer that is at least three times the size of the spot diameter.

According to some embodiments, the laser beam is configured to be rotated at a rotational velocity of 1.5-2.5 mm/sec. According to some embodiments, the laser beam is configured to be rotated at a rotational velocity of about 2 mm/J.

According to some embodiments, the fixed distance between the catheter's laser transmitting element and the duodenal wall is in the range of 15-30 mm.

According to some embodiments, fixed distance between the catheter's laser transmitting element and the duodenal wall is in the range of 20-25 mm.

According to some embodiments, the ablative dose is determined by the distance between the catheter's laser transmitting element and the duodenal wall, the rotational velocity of the laser beam and the laser beam's power.

According to some embodiments, there is provided a device for selectively ablating a submucosal layer of a duodenal wall and/or of sensory neurons therein, the device comprising a catheter including: a laser transmitting element coupled with the catheter body and configured to transmit a laser beam having a spot diameter of less than 200 microns and to provide an ablative dose of 0.5-2.5 J/mm; wherein the laser beam is configured to selectively ablate an area of the submucosal layer that is at least twice the size of the spot diameter, while essentially preventing damage of the surrounding mucosal, muscularis and/or serosal layers of the duodenal wall; a deflective optical element functionally coupled with the laser emitting element and configured to direct the laser beam to the submucosal layer; and an expandable member configured to stretch the duodenal wall and to generate a fixed distance between the laser transmitting element and the duodenal wall.

According to some embodiments, the laser transmitting element includes or is a single mode optical fiber.

According to some embodiments, the laser transmitting element has a core diameter of 8-10 microns.

According to some embodiments, the laser beam has a wavelength of 1550 or 1567 nm.

According to some embodiments, the laser beam has a spot diameter of 100 microns or less.

According to some embodiments, the laser beam is configured to selectively ablate an area of the submucosal layer that is at least three times the size of the spot diameter.

According to some embodiments, the deflective element is rotatable and configured to rotate the laser beam at a rotational velocity of 1.5-2.5 mm/sec.

According to some embodiments, the deflective element configured to rotate the laser beam is configured to be rotated at a rotational velocity of about 2 mm/J.

According to some embodiments, the expandable member is configured to stretch the duodenal wall such that the fixed distance between the catheter's laser transmitting element and the duodenal wall is in the range of 15-30 mm.

According to some embodiments, the expandable member is configured to stretch the duodenal wall, such that the fixed distance between the catheter's laser transmitting element and the duodenal wall is in the range of 20-25 mm.

According to some embodiments, the expandable member is a non-compliant balloon.

According to some embodiments, the ablative dose is determined by the distance between the catheter's laser transmitting element and the duodenal wall, the rotational velocity of the laser beam and the laser beam's power.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some, or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

The patent or application file contains at least one drawing executed in color. Copies of this patent or patent application publication with color drawing(s) will be provided by the Office upon request and payment of the necessary fee.

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION OF THE INVENTION

Figure 1:
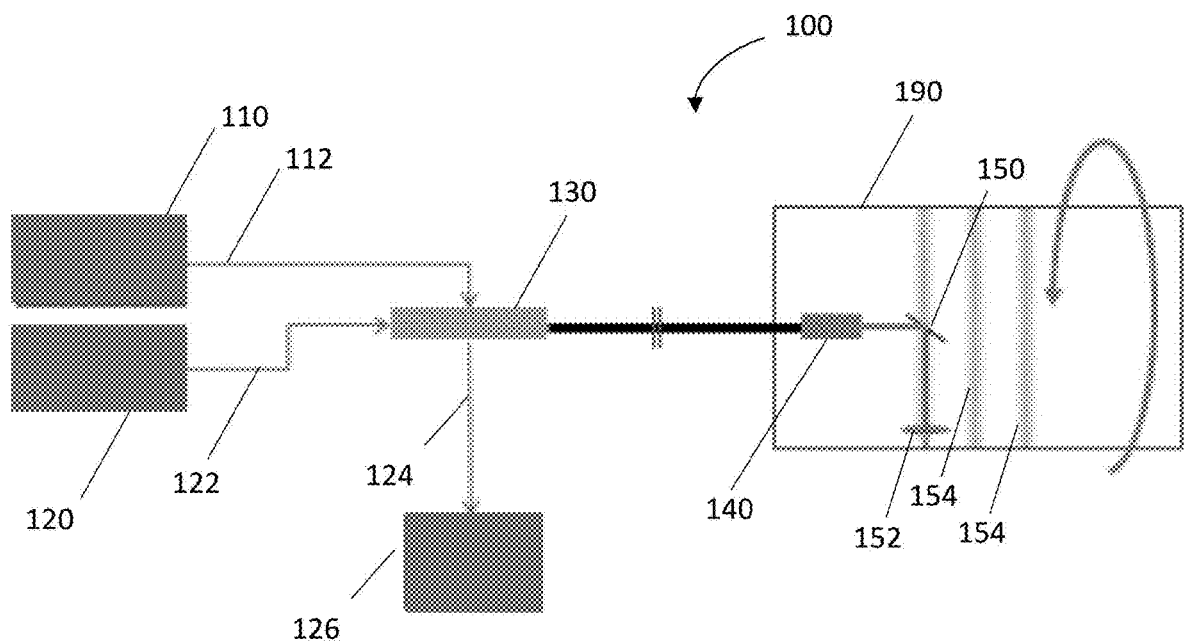
FIG. 1 is an outline of an optical system for ablation of duodenal tissue with real-time ablation feedback, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, there is provided a device for ablation of the duodenal submucosal layer, the device including a catheter comprising an expandable member configured to stretch the duodenal wall and to generate a fixed distance between a center of the catheter and the duodenal wall; and a laser transmitting element coupled with the catheter body and configured to transmit an ablative laser beam to the submucosal layer. According to some examples, a CW laser in the range of 1550-1570 nm may be used. The laser beam may be configured to generate a spot diameter of less than 100 micron and to provide an ablative dose in the range of 0.5-3.5 J/mm, the dose determined by the distance between the laser transmitting element and the tissue (i.e. radius of the balloon), the rotational velocity of the deflected beam and the power of the laser. Advantageously, the device is configured to ablate, denervate and/or otherwise modify the submucosal layer and/or sensory neurons therein, while leaving the surrounding mucosal, muscularis and/or serosal layers of the duodenal wall.

As used herein, the term "duodenum" refers to the part of the small intestine of a vertebrate's gastrointestinal tract which is situated between the stomach and the jejunum. According to some embodiments, the duodenum comprises the pylorus of the stomach. The duodenum includes the lumen and the duodenal wall surrounding the lumen. The duodenal wall includes the following layers from the lumen outwards: the mucosa villi layer, the submucosa layer (which includes the submucosal plexus, the circular muscle layer, the myentric plexus), the longitudinal muscle layer and the peritoneum/mesenteric layer. The combination of the circular muscle layer and longitudinal muscle layer may be referred to herein as the tunica muscularis or muscularis.

As used herein, the terms "submucosal plexus" and "Meissner's plexus" may be used interchangeably and refer to a neural plexus residing in the submucosa layer of the duodenal wall. Without being bound by any theory, the submucosal plexus transmits neural signals within the duodenum, e.g. to nerves extrinsic to the duodenum, such as the vagus, duodenal ganglia, sympathetic nerves, and parasympathetic nerves. The submucosal plexus comprises mainly sensory neurons that transmit neural signals obtained from chemical and/or mechanical sensors in the duodenum activated by passage of food through the duodenum.

According to some embodiments, a target region is a region within the duodenal wall that contains sensory neurons. According to some embodiments, the target region includes at least part of the neurons within regions selected from the group consisting of: the myentric plexus, the submucosal plexus, duodenal branches of the vagus nerve, sympathetic nerves innervating the duodenal wall, parasympathetic nerves innervating the duodenal wall, VAN arrays in the duodenal wall and a combination thereof. Each possibility represents a separate embodiment of the present disclosure.

As used herein, the term "catheter" refers to a catheter which is configured to be introduced into the lumen of a duodenum. According to some embodiments, the catheter is configured to be introduced into the lumen of a duodenum through the mouth of a subject. According to some embodiments, the catheter is configured to be introduced through the colon. According to some embodiments, the catheter comprises an endoluminal duodenal catheter. According to some embodiments, the catheter is an endoluminal duodenal catheter. According to some embodiments, the catheter is a laser emitting catheter. According to some embodiments, the laser element is comprised in, and possibly located within, the catheter.

As used herein, the term "ablation" may refer to affecting tissue, by vaporization, chipping, cutting, impacting, denervating, modifying, damaging, severing or other erosive processes or combination of processes, or otherwise impeding at least part of the neurons in the target area. Each possibility is a separate embodiment. According to some embodiments, ablation may refer to a process during which damage is caused to duodenal tissue and/or sensory nerves within the duodenal tissue, by transmitting laser radiation thereon. According to some embodiments, the ablation comprises thermal damage. According to some embodiments, the ablation comprises mechanical damage. According to some embodiments, the ablative laser radiation may be configured to heat the target region to at least 45-75° C. or significantly higher when exposure is very short to induce a more significant injury. According to some embodiments, the ablation may impact neurohormonal and/or other signals triggered by food passing through the gastrointestinal (GI) tract, and thus the subject's sense of satiety and/or hunger and/or hormonal secretion.

According to some embodiments, the ablative laser radiation may be pulsed laser radiation. According to some embodiments, the ablative laser radiation may be focused on a target area comprising sensory neurons. According to some embodiments, tissue surrounding the target region may remain functional.

According to some embodiments, the laser beam may be configured to be transmitted in a direction essentially perpendicularly to the longitudinal axis of the catheter, for example, using a prism, a mirror or other suitable deflective element. According to some embodiments, the deflective element, functionally coupled with the laser emitting element, may be configured to direct the laser beam to a region on and/or beneath the duodenal wall. According to some embodiments, the deflective element (e.g. prism or mirror) may be rotatable so as to bring about a circumferential ablation. As used herein, the term "circumferential ablation" or "ablation along a circumferential trajectory" may be used interchangeably and may refer to ablation provided around the duodenal wall. According to some embodiments, the circumferential ablation may be circular, i.e. if the laser beam is rotated 360 degrees without movement of the catheter and/or laser emitting element. According to some embodiments, the circumferential ablation may be helical, i.e. if the laser beam is rotated concurrently with forward (or backward) movement of the catheter and/or laser emitting element.

According to some embodiments, the deflective element may deflect the laser beam at an angle of 90 degrees from a longitudinal axis of the catheter. According to some embodiments, the deflective element deflects the laser beam through one or more apertures in the catheter. According to some embodiments, the deflective element may be located within the distal head of the catheter. According to some embodiments, the deflective element may be associated with or be an integral part of the laser transmitting element. According to some embodiments, the deflective element may be rotatable. According to some embodiments, the deflective optical element may direct the laser radiation to a plurality of target areas along a circular trajectory within the duodenal wall or in contact with the duodenal wall. Each possibility is a separate embodiment. According to some embodiments, the deflective element may be or include a prism, optionally a rotatable prism. According to some embodiments, the deflective element may be or include a beam-splitter prism. According to some embodiments, the device may further include at least one lens element. According to some embodiments, the lens element is or includes a correction lens configured to correct aberration.

According to some embodiments, the deflective optical/ element may be selected from the group consisting of a wide-angle lens, a dove prism, a reversion or "K" prism, a Delta or Pechan prism, a dispersive prism, a reflective prism, a beam-splitting prism, a deflective prism, a triangular prism, a trapezoidal prism, a Glan-Taylor prism or a Glan-laser prism, a high-powered laser-light right-angle prism, a retroreflector and combinations thereof. Each possibility is a separate embodiment. According to some embodiments, the prism is a low-loss deflective prism. According to some embodiments, the dispersive prism is a triangular, a Pellin-Broca prism, an Abbe Prism or a compound prism. According to some embodiments, the optical element may be a wide-angle lens system capable of correcting f-theta distortion or f-sin(theta) distortion. According to some embodiments, the system further includes a focusing element, optionally positioned before the rotatable optical element, with long enough focal length to enable focusing on a target.

According to some embodiments, the ablative laser radiation is a pulsed laser radiation configured to initiate non-linear energy absorption and interaction with the tissue. Without wishing to be bound by any theory or mechanism, short pulsed focused laser radiation directed at a tissue may result in a non-linear interaction with the tissue, such that plasma formation and/or photo-ablation occur only at a site in the tissue in which the energy peak at a given area has an energy flux high enough to cross a pre-determined threshold. According to some embodiments, photo-ablation in the presence of a high enough peak power in the focus area may be accompanied with some level of absorption of the laser beam by adjacent tissue. Non-limiting examples of lasers that may be used to produce such laser radiation include micro Q-Switched Nd:YAG lasers such as, but not limited to, those manufactured by Kigre (MK-367) that are very compact and produce a beam that may cross ablation threshold when sufficiently focused, standard flash pumped Q-Switched lasers (including those that are self Q-Switched), high repetition rate Solid Sate Diode Pumped Nd:YAG lasers, fiber lasers which use small spots to obtain a high enough peak power to cause damage, or any combination thereof. Each possibility is a separate embodiment. Other non-limiting examples include CW, quasi CW or Q switched lasers. Appropriate lasers can be, for example, double YAG in 532 nm, or laser diode of 980 nm or 808 nm, a laser in the 1500 nm range or Holmium/Thuliium lasers at 2 microns.

According to some embodiments, the ablative beam may have a wavelength in the 1300 nm, 1400 nm, 1450-1600 nm, 1530-1590 nm, 1550-1570 nm, 980-1064 nm or 1850-1950 nm range. As a non-limiting example, the ablative beam may have a wavelength of 1550 nm. As another non-limiting example, the ablative beam may have a wavelength of 1064 nm. As another non-limiting example, the ablative beam may have a wavelength of 1067 nm.

According to some embodiments, ablation may be performed using a single mode laser (SM). According to some embodiments, ablation may be performed using a multi-mode laser (MM). According to some embodiments, the SM ablation fiber may be coupled to a core fiber with a controlled/limited increase in beam diameter, i.e., an increase from ~10 micon to 50-200 micron decreasing the beam divergence. According to some embodiments, M-squared increases by no more than times 3-5. According to some embodiments, the single mode optical fiber may have a typical core diameter of 8-10 microns.

According to some embodiments, the laser beam may have a spot diameter of less than 200 microns, less than 150 microns, less than 100 microns, less than 50 microns, or less than 20 microns. Each possibility is a separate embodiment.

According to some embodiments, the laser beam may provide an ablative dose of 0.2-3.5 J/mm, 0.5-2.5 J/mm, 0.5-2.0 J/mm, 1.0-2.0 J/mm or any other suitable range within of 0.2-3.0 J/mm. Each possibility is a separate embodiment. As a non-limiting example, the ablative dose may be 1.7 J/mm.

As used herein, the term "ablative dose" refers to a dose of ablative energy provided to the target tissue at the point of impact. According to some embodiments, the ablative dose may be determined according to the laser power, the rotational velocity of the beam (the slower the beam rotates the larger the dose at a certain point of impact), and the distance to the duodenal wall (as determined by the expandable member).

According to some embodiments, the laser beam may be a 1550-1567 nm CW laser beam with a laser power of 2-20 Watts (W) e.g. 3-4 W or any other suitable laser power. As a non-limiting example, 3.6 W can be used with a rotation velocity of 2 mm/sec, which results in a dose of 1.8 J/mm. This indicates ~40 sec per turn in a 25 mm diameter balloon for spot diameters of 100 micron or less which ensures a sufficiently high ablative dose. As another non-limiting example, using a laser power of 15 Watt, the rotational velocity may be significantly higher, e.g. a circumferential ablation line may be completed in <10 sec for the same dose (1.8 J/mm) and spot diameter (i.e. 100 microns or less). According to some embodiments, when larger spots are generated (e.g. >300 micron), a smaller dose of laser energy must be provided (e.g. by decreasing laser power and/or by increasing velocity) in order to avoid uncontrolled collateral damage.

According to some embodiments, the rotational velocity of the laser beam may be in the range of 0.5-30 mm/sec, 1-3 mm/sec, 1.5-2.5 mm/sec or any other suitable rotational velocity within the range of 0.5-30 mm/sec for different laser powers. For example, for 3.6 W, a velocity of 12 mm/sec of the deflected beam rotated over the duodenum would result in 0.3 J/mm and a 0.83 mm/sec would result in 3 J/mm. For a 15 Watt beam, a rotation of the beam at 5 mm/sec would result in 3 J/mm while rotation at 30 mm/sec would result in 0.5 J/mm. Each possibility is a separate embodiment. As a non-limiting example, the rotational velocity may be 2 mm/sec.

According to some embodiments the ablation lines are created when the duodenum is expanded/stretched to a diameter of 25-70 mm. According to some embodiments, the diameter is determined by a non-compliant balloon that stretches the duodenum. According to some embodiments, semi or complaint balloons may be used in conjunction with means to determine the diameter so as to ensure that the desired dose may be determined and/or adjusted by modulation of laser power and/or rotational speed.

According to some embodiments, the distance of the laser rotating element to the duodenal wall, the balloon radius, may be 12.5-25 mm, 15-30 mm, 18-25 mm or any other suitable distance within the range of 12.5-35 mm. Each possibility is a separate embodiment. As a non-limiting example, the distance may be 18 mm.

According to some embodiments, the gap between the ablation lines may be in the range of 2-15 mm, 3-10 mm, 4-8 mm or 5-7.5 mm. Each possibility is a separate embodiment.

According to some embodiments, the laser emitting element may further include a second optical fiber, configured to transmit a second, evaluative/feedback beam. According to some embodiments, the fiber configured to transmit the ablative radiation may have a smaller core than the fiber used for the feedback radiation, such that the spot diameter of the feedback radiation on the tissue will be larger than the spot diameter of the ablative radiation.

According to some embodiments, the laser emitting element may include a double clad fiber configured to deliver the ablative laser beam through the core and the evaluative/feedback laser beam through the clad. According to some embodiments, the laser emitting element may include a double clad fiber configured to deliver the first, ablative laser beam, and the second evaluating beam through the core and sense/read the back reflection of scatter of the evaluative laser beam through the clad.

According to some embodiments, the feedback beam may enable monitoring and/or identifying of at least one parameter related to the ablation of the duodenal tissue. Non-limiting examples of suitable parameters which may be evaluated, monitored and/or identified by the feedback beam include: effect of ablation, abnormalities and/or dysfunction in the ablation process (e.g. improper expansion of the expandable member, improper termination of the laser treatment, impaired rotation of the beam etc.), velocity of beam rotation, diameter of expanded section (e.g. by measuring the diameter of the expandable member once expanded), identification of a previous section that underwent ablation, for example, in order to align repositioning of the expandable member for repetitive interventions, identification of undesired tissue, such as, but not limited to, papilla or any other suitable parameter or combination of parameters. Each possibility is a separate embodiment.

Additionally or alternatively, the evaluation of the ablation may include collection of the back reflected and/or scattered light originating from the ablative laser beam itself, optionally obviating the need for an additional laser and/or optical fiber. According to some embodiments, the feedback may include operating the laser transmitting element in a first, ablative mode and then operating the laser transmitting element in a second, evaluating mode, configured to detect and/or collect back reflected and/or scattered radiation. According to some embodiments, the feedback can be based on the amplitude of a reflected beam and/or phase shift and/or noise spectrum and/or noise within a pre-set frequency range, and/or deviation from a pre-set range associated with its reflection/scattering.

According to some embodiments, the ablative laser beam may have a same or a different spot diameter on the tissue, as compared to the second, evaluative laser beam.

According to some embodiments, the ablative laser beam and the feedback beam may be laterally separated by using two optical fibers configured to provide offset laser beams. According to some embodiments, a laser transmitting element may include a separating element, such as, but not limited to, a lens configured to increase the angular spacing e.g. by 500-5000 micron, or 700-3000 micron, when reaching the duodenal wall (approximately 10-25 mm from the center of the catheter). According to some embodiments, the ablative laser beam and the feedback beam may be angularly separated. According to some embodiments, the ablative and feedback laser beams may be overlapping beams angularly separated using a separating element, such as, but not limited to, a dispersive element, a diffractive optical element, a prism or other suitable element configured to selectively separate the first (ablative) and second (feedback) laser beams. According to some embodiments, the distance between the ablation spot and the feedback spot may be determined by the type of separating element used. According to some embodiments, the overlapping beams may be transmitted by two separate optical fibers. According to some embodiments, the overlapping beams may be transmitted by a double cladded fiber.

According to some embodiments, the device may further include a rotating shaft configured to rotate the catheter and/or the laser transmitting element or parts thereof (e.g. the deflective element), during the ablation procedure.

According to some embodiments, the expandable member may be a balloon. According to some embodiments, the balloon may be semi-compliant or non-compliant. According to some embodiments, the balloon may expand the duodenum to a predetermined radius (using a non-complaint balloon) or to a pre-set range of diameters (using semi-complaint balloons), while complying with the shape of the duodenum lumen, along its longitudinal axis. The lack of compliancy of the balloon may be crucial in order to ensure that a pre-determined dose of laser energy be used regardless of angular orientation of the laser beam, such that a uniform ablation across the duodenal surface is obtained. This since, the semi/non-compliant balloon ensures that the rotating beam is derived from the center of the balloon and thus of the duodenum.

According to some embodiments, the balloon, or other expandable member, may include multiple sections. According to some embodiments, the sections of the balloon may be interconnected by connection points allowing bending (e.g. 120 degrees bending) between sections, so as to enable expansion of the duodenum lumen, while maintaining its 3D shape. According to some embodiments, the segments may be of a same or different lengths and/or diameters to comply with anatomy. According to some embodiments, the angle of balloon wall between segments may be minimized to 15 degrees (+/−5 degrees) to decrease "dead area" between the segments, as illustrated hereinbelow. According to some embodiments, the connection points (also referred to as bending sites) may serve as landing/support zones or axial sites for the rotating shaft.

According to some embodiments, the balloon (or optionally sections thereof) may be coated with parylene to increase thermal resistance, to deal with heating effects on the tissue exposed to the ablating laser beam, thus protecting the balloon from being damaged.

According to some embodiments, the balloon may include longitudinal lines configured to enable determining the rotational speed of the first and/or second laser beam and/or the diameter of the balloon. According to some embodiments, the angular velocity of the ablative beam may be determined by measuring the modulation frequency of the feedback obtained from those lines upon rotation. According to some embodiments, the longitudinal lines may be positioned at an external or internal surface of the balloon. According to some embodiments, the longitudinal lines may be made of metal, dyes, thermal based marks or other material that does not expand, in order to ensure that the longitudinal lines maintain a constant width required to enable determination of balloon diameter.

According to some embodiments a semi-compliant or a compliant balloon maybe used instead on non-compliant balloon to enable larger flexibility regarding the balloon diameter. This may enable using lower profile catheters as a less stretched balloon, when compressed, can be accommodated in a smaller profile catheter than a large PET balloon that can expand to 30-50 mm in diameter. Accordingly, means are required to determine the diameter of the extended balloon at the target to make sure the desired dose of ablation is applied.

According to some embodiments, the balloon may include circumferential lines (width bands) configured to determine the linear velocity of the catheter and/or of the laser transmitting element.

According to some embodiments, interruption and/or divergences in the signal obtained from back reflection of radiation from the longitudinal and/or circumferential lines may be used to detect rotational impairment, balloon malfunction, malfunctioning optics or any other suitable parameter or combination of parameters.

According to some embodiments, radiation, back-reflected from longitudinal and/or circumferential lines, may be used to calibrate the intensity of a laser beam used for ablation. According to some embodiments, free-space or fiber beam splitters may be used. In such case, one of the channels that does not get to the sample can be used for calibration. Additionally or alternatively, imaging elements such as CMOS or CCD cameras may be used to detect impeded and/or halted rotation of the beam, by detecting a frozen video signal.

Reference is now made to FIG. 1, which is an outline of an optical system 100 for ablating duodenal tissue (or other lumen in the GI or pulmonary tract), with real-time ablation feedback, according to some embodiments. System 100 includes a laser 110 configured to emit a laser beam 112 which is configured to cause ablation of tissue upon which it impinges, while causing minimal damage to the surrounding mucosal, muscularis and/or serosal layers of the duodenal wall. Laser beam 112 may, for example, have a wavelength of about 1550 or 1567 nm and a power of about 3.6 W and is configured to generate a spot having a diameter of 200 microns or less, preferably 100 microns or less. Optionally, system 100 may also include a second laser 120 configured to emit a second laser beam 122, the backscattered light of which enables evaluation of tissue modifications caused by the ablation. Second laser beam 122 may, for example, have a wavelength of about 980 nm and a fixed power density on the target. Laser beam 112 and second laser beam 122 are directed to a first optical element, here wavelength-division multiplexing (WDM) system 130, which multiplexes a number of optical carrier signals onto a single optical fiber and demultiplexes (splits them apart) at exit. WDM 130 enables bidirectional communications and thus enables receiving part of second laser beam 122 back reflected from the tissue, and to send, as illustrated by arrow 124, the reflected beam to a sensor 126 configured to detect the intensity thereof. When exiting WDM system 130, laser beam 112 and second laser beam 122 reach a second optical element, also referred to herein as a laser transmitting element 140. Laser transmitting element 140 is optionally configured to generate a spatial separation between laser beam 112 and second laser beam 122, thus enabling a delay between the ablative laser beam 112 and the feedback beam 122. The beams are subsequently deflected using a third, deflective optical element 150 (such as, but not limited to, a mirror or a prism), configured to deflect laser beam 112 and second laser beam 122 at an angle of essentially 90 degrees, whereafter they are focused on a target area in the duodenal wall (illustratively depicted as box 190), by lens 152. Importantly, in order to satisfy a 1.8 mm maximal diameter of the optical fiber, and in order to maximize the spatial separation between the beams, laser transmitting element 140 should preferably be positioned before deflective element 150. Deflective element 150 may be rotatable, such that laser beam 112 and second laser beam 122 are deflected circumferentially around the duodenal wall, such that first laser beam 112 generates ablative lines 154. According to some embodiments, deflective element 150 may have a rotational velocity of approximately 2 mm/sec, as essentially described herein.

Figure 2A:
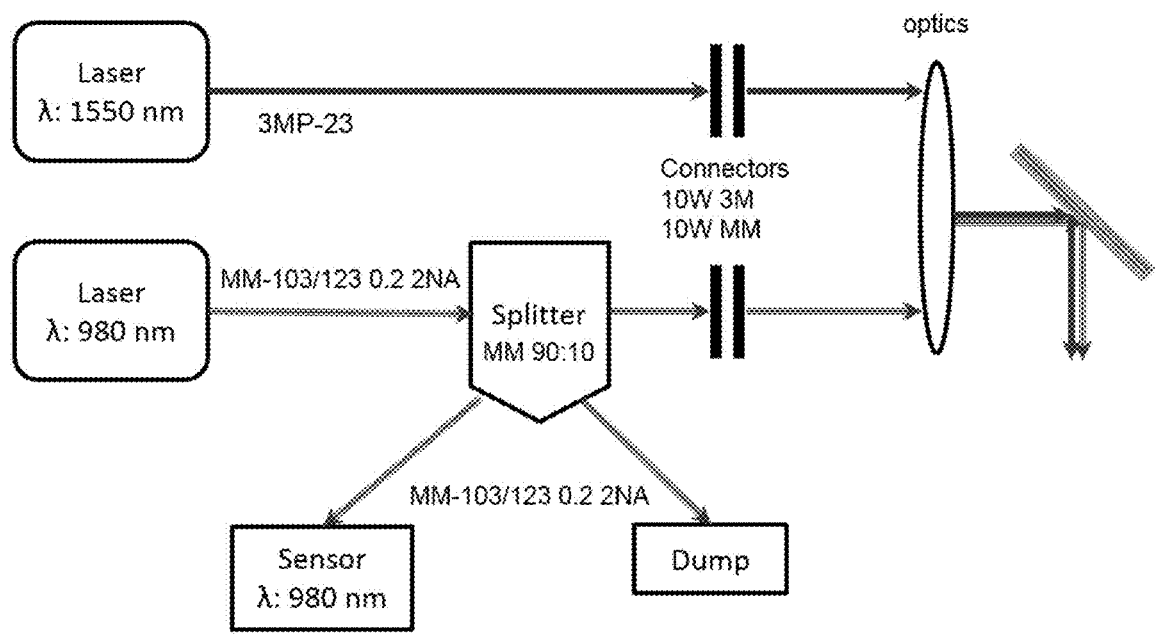
FIG. 2A schematically depicts a setup utilizing two separate optical fibers for delivering the ablative and the feedback beams, according to some embodiments.
Figure 2B:
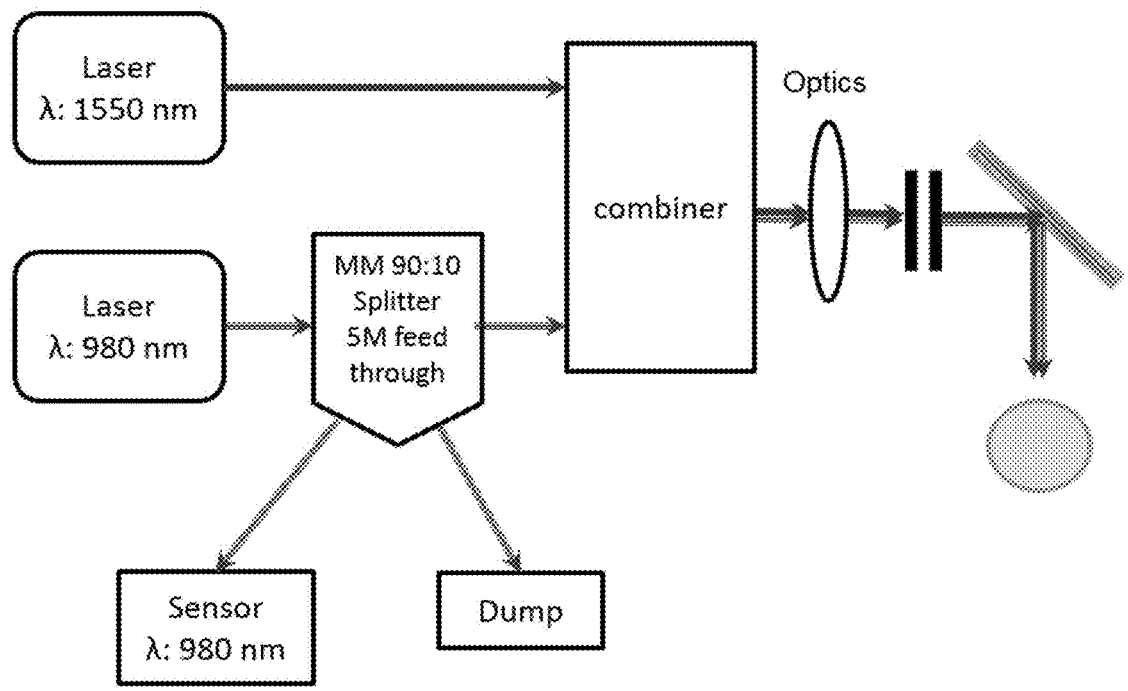
FIG. 2B schematically depicts a setup utilizing a combiner (e.g. a double cladded optical fiber), according to some embodiments.

Reference is now made to FIG. 2A and FIG. 2B, which illustratively depicts a setup 200a suitable when using two separate optical fibers for delivering the ablative and the feedback beams, and a setup 200b suitable when using a combiner (e.g. a double cladded optical fiber), respectively. According to some embodiments, a significant difference in spot diameter between the ablative beam and the feed beam is more easily achieved using separate optical fibers, as depicted in setup 200a as compared to setup 200b.

Figure 3:
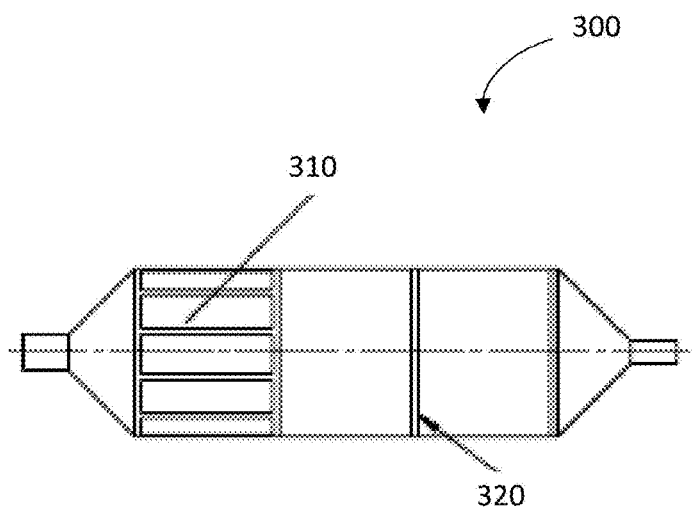
FIG. 3 schematically illustrates a balloon configured to stretch and/or widen the duodenum to a predetermined diameter or range of diameters, according to some embodiments.

Reference is now made to FIG. 3, which schematically illustrates an expandable member, here a balloon 300, configured to stretch and/or widen the duodenum to a predetermined diameter or range of diameters, according to some embodiments. According to some embodiments, balloon 300 may include longitudinal marks 310. Longitudinal marks 310 may be configured to enable determining the rotational speed of the laser beam and/or the diameter of the balloon. According to some embodiments, longitudinal lines 310 may be positioned at an external or internal surface of the balloon. According to some embodiments, the longitudinal lines may be made of metal, dyes, thermal based marks or other material that do not expand, in order to ensure that the longitudinal lines maintain a constant width required to enable determination of balloon diameter. According to some embodiments, balloon 300 may further include circumferential lines (width bands) 320 configured to determine the linear velocity of the catheter and/or of the laser transmitting element. According to some embodiments, balloon 300 may be coated with parylene to increase thermal resistance, to deal with heating effects on the tissue exposed to the ablating laser beam, and/or to direct the laser beam.

Figure 4:
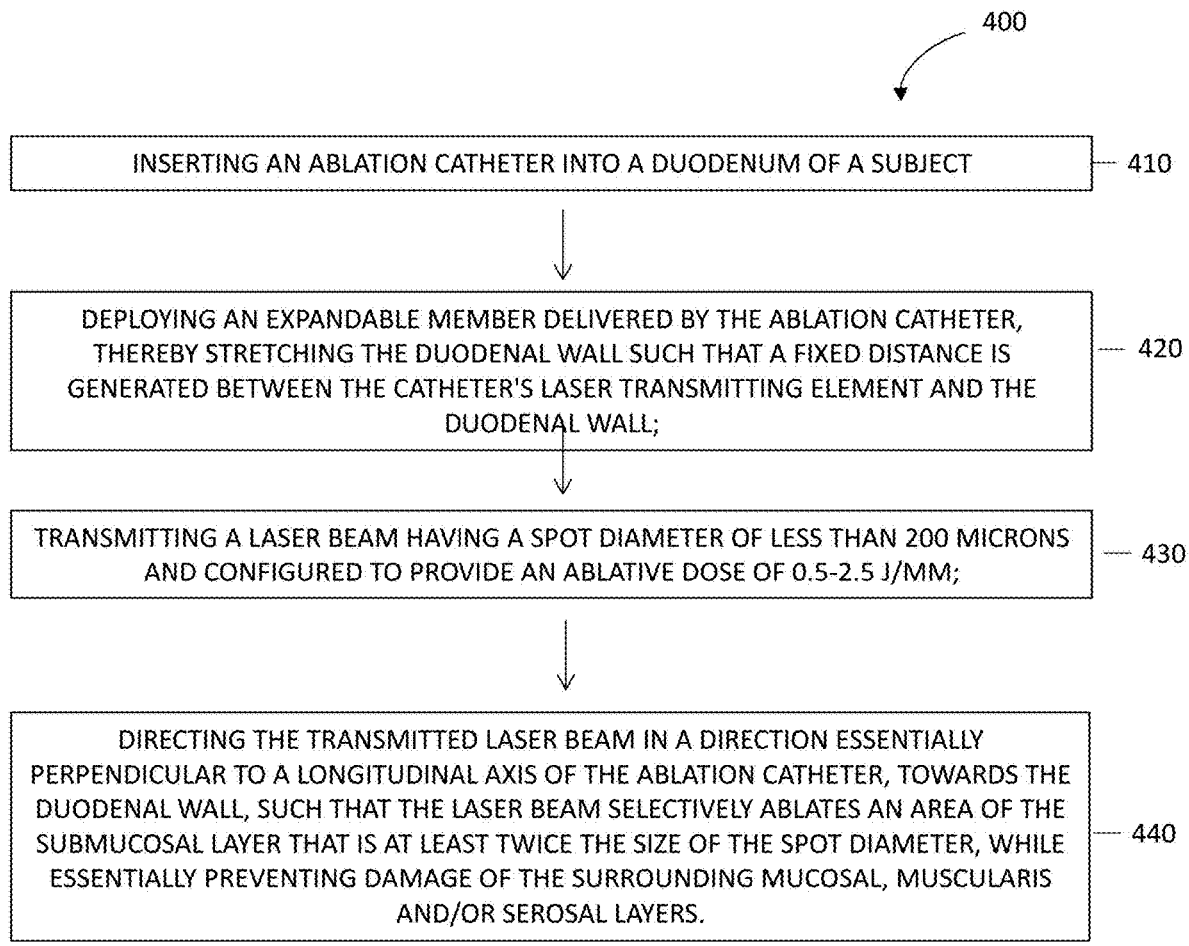
FIG. 4 is an illustrative flow chart of a method for optimized ablation of the submucosal layer of the duodenum and/or of sensory neurons therein, according to some embodiments.

Reference is now made to FIG. 4, which is an illustrative flow chart of a method 400 for selectively ablating a submucosal layer of a duodenal wall and/or of sensory neurons therein, according to some embodiments.

In step 410 an ablation catheter is inserted into a duodenum of a subject and in step 420 an expandable member delivered by the ablation catheter is deployed, thereby stretching the duodenal wall, such that a fixed distance between the catheter's laser transmitting element and the duodenal wall is generated. After positioning, a laser beam having a spot diameter of less than 200 microns and configured to provide an ablative dose of 0.5-3.5 J/mm is transmitted (step 430). The ablative dose is determined by the distance between the catheter's laser transmitting element and the duodenal wall, the rotational velocity of the laser beam and the laser beam's power. In step 440, which may be concurrent with step 430, a rotatable deflective element directs the transmitted laser beam in a direction essentially perpendicular to a longitudinal axis of the ablation catheter, towards the duodenal wall. The deflective element is rotatable and configured to rotate the laser beam at a rotational velocity of 1.5-2.5 mm/sec, such that the ablation is performed along a circumferential trajectory of the duodenal wall. As a result, the laser beam selectively ablates an area of the submucosal layer that is at least twice the size of the initial spot diameter, while at the same time essentially preventing damage of the surrounding mucosal, muscularis and/or serosal layers of the duodenal wall.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of".

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

EXAMPLES

Example 1—In-Vivo Ablation of Pig Duodenum Using a Multi-Mode (MM) Optical Fiber Generating a Large Spot Diameter In-vivo tissue ablation of the submucosa of a domestic pig duodenum was performed using a 1567 nm, 3.6 W MM optical fiber generating a spot diameter of approximately 500 microns. The ablation was performed at a rotational speed of 12 mm/sec, i.e. approximately 6.5 sec for completing a whole circumferential ablation of the duodenal wall which was stretched by a non-compliant balloon, such that the diameter of the ablated circles generated by the emitting optical fiber was approximately 25 mm, thus providing an ablative dose of 0.3 J/mm.

Figure 5:
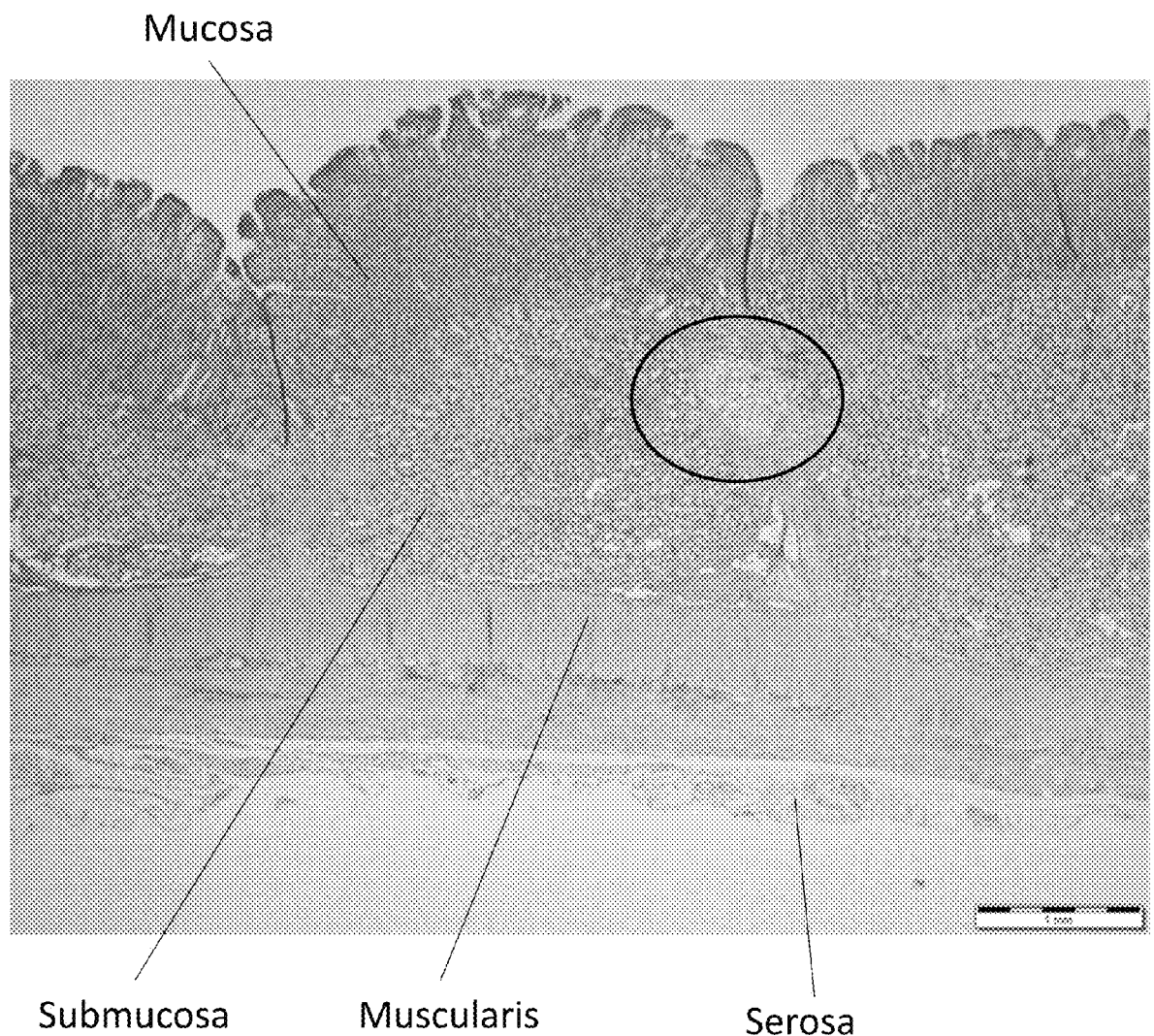
FIG. 5 shows a representative histological staining of duodenal tissue 2 weeks after an ablative treatment using a multi-mode optical fiber.

As seen from FIG. 5, which shows a representative histological staining of the treated duodenal tissue, 2 weeks after treatment, the ablation caused a modification of the mucosal tissue in an area corresponding to the point of impact (encircled), i.e. to the spot diameter of 500 microns, and only little lateral modifications were observed (total area of impact less than 1 mm$^2$). Advantageously, no significant damage to the surrounding layers (mucosa, muscularis and serosa) was observed.

Example 2—In-Vivo Ablation of Pig Duodenum Using a Single-Mode (SM) Optical Fiber Generating a Small Spot Diameter In-vivo tissue ablation of the submucosa of a domestic pig duodenum was performed using a 1550 nm, 3.6 W SM optical fiber generating a spot diameter of less than 100 microns. The ablation was performed at a rotational velocity of 2 mm/sec while the duodenal wall was stretched by a non-compliant balloon, such that the diameter of the ablated circles generated by the emitting optical fiber was approximately 20 mm, thus providing an ablative dose of 1.8 J/mm.

Figure 6:
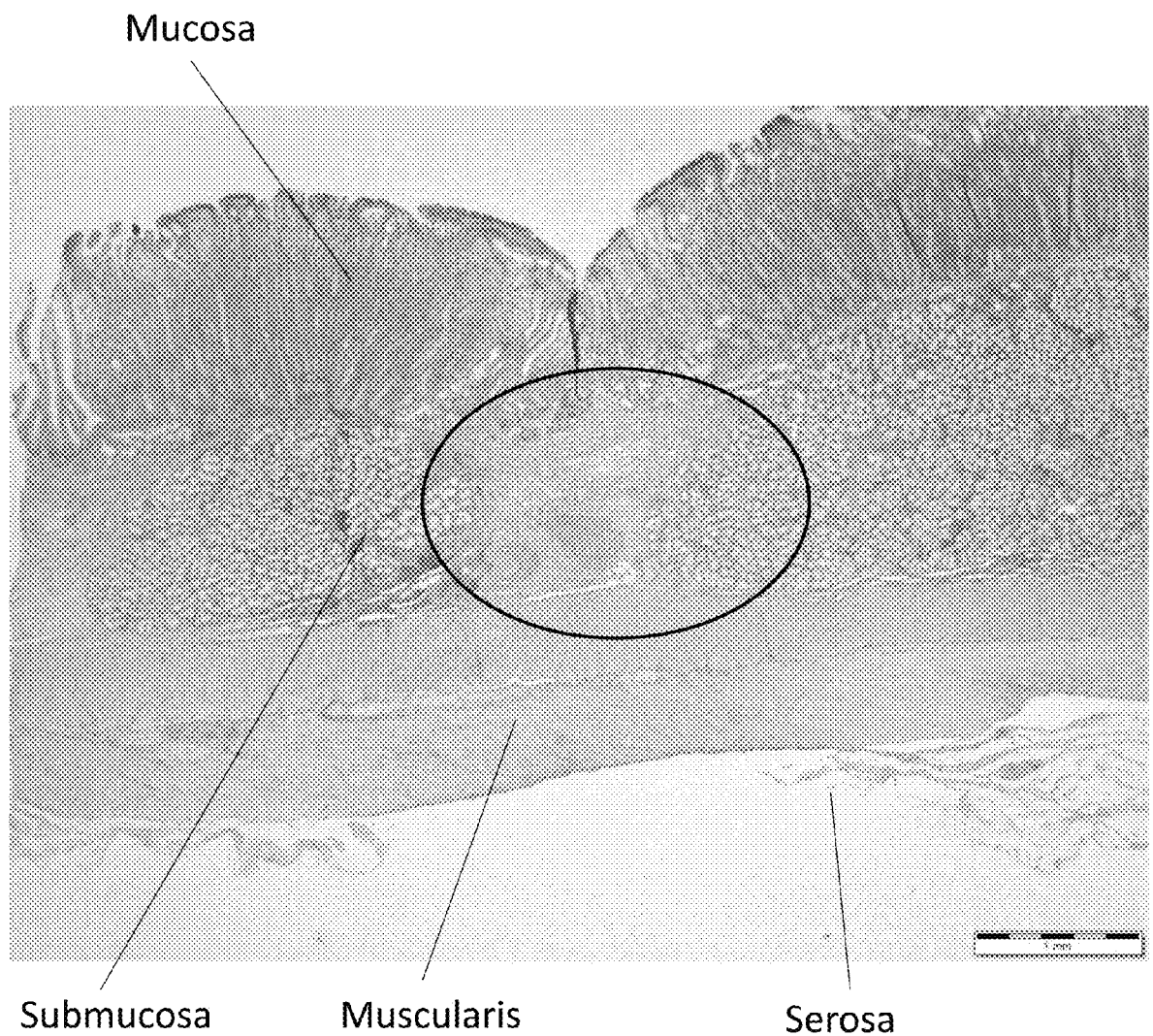
FIG. 6 shows a representative histological staining of duodenal tissue 2 weeks after an ablative treatment using a single-mode optical fiber.

As seen from FIG. 6, which shows a representative histological staining of the treated duodenal tissue, 2 weeks after treatment, the ablation surprisingly caused a modification of the mucosal tissue in an area (encircled) significantly larger than the initial point of impact, i.e. significantly larger than the spot diameter of less than 100 microns. That is, a wide lateral modification of adjacent submucosal tissue was observed (total area of impact ~1 mm$^2$). It was thus surprisingly found that the small laser spot of SM optical fiber yielded a wider effect on the submucosal target tissue than that obtained using a MM optical fiber with a larger spot diameter. Advantageously, despite the lateral spread of the impact, no significant damage to the surrounding layers (mucosa, muscularis and serosa) was observed.

Figure 7:
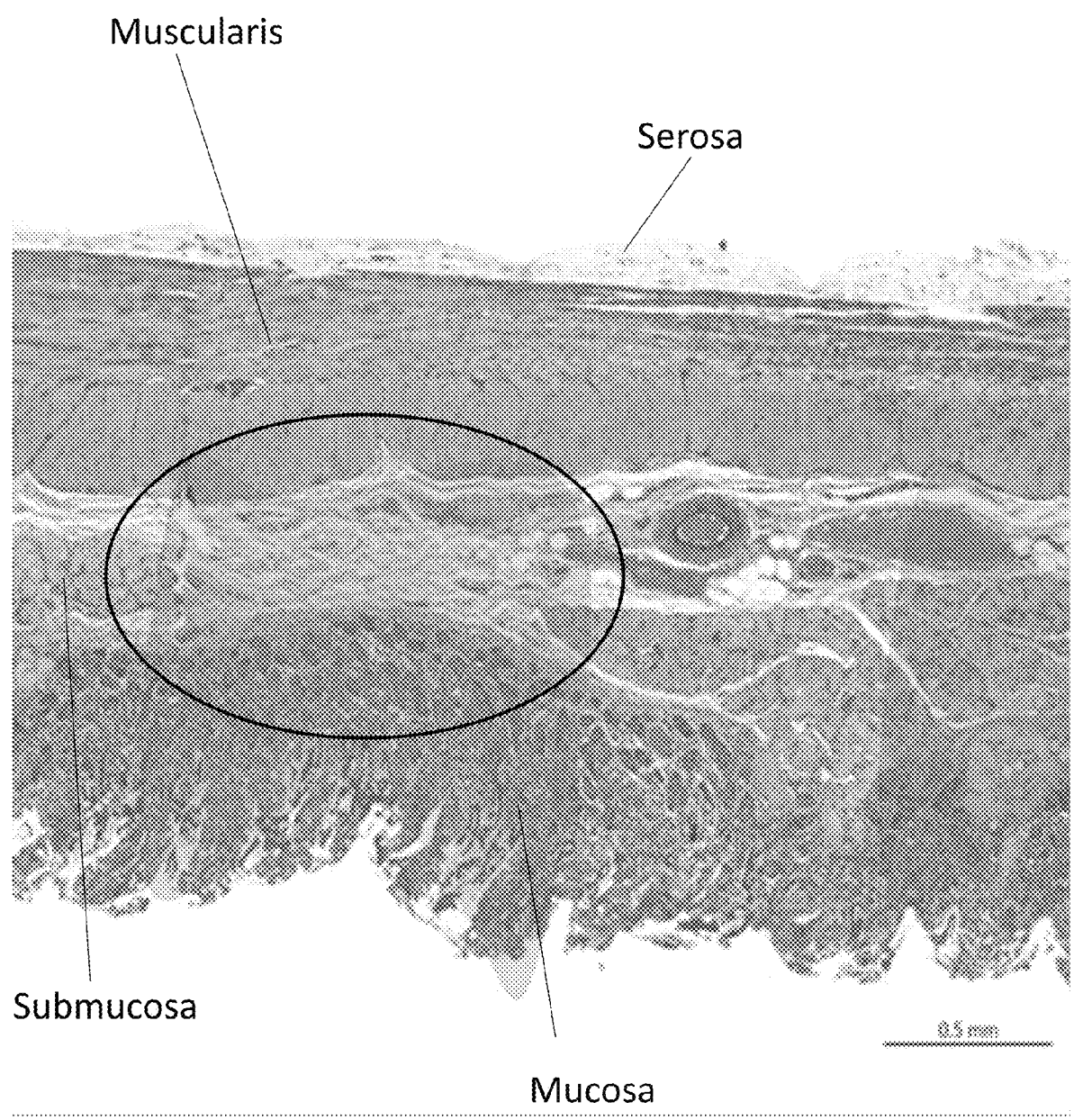
FIG. 7 shows a representative histological staining of duodenal tissue 2 months after an ablative treatment using a single-mode optical fiber.

Similarly, as seen from FIG. 7, which shows a representative histological staining of the treated duodenal tissue, 2 months after treatment, a modification of the mucosal tissue in an area (left encircled area) was again observed as being significantly larger than the initial point of impact, i.e. significantly larger than the spot diameter of less than 100 microns (total area of impact ~1 mm$^2$), while no significant damage to the surrounding layers (mucosa, muscularis and serosa) was observed.

These results suggest that a cascade of damage induced by the significant impact of the highly localized laser beam (spot diameter of 100 microns or less) with high peak power, increases the probability that the effect caused to the submucosal layer will be sustainable, while collateral damage is minimized.

Example 3—In-Vivo Ablation of Pig Duodenum Using a Single-Mode (SM) Optical Fiber Generating a Small Spot Diameter In-vivo tissue ablation of the submucosa of a domestic pig duodenum was performed using a 1550 nm, 3.6 W SM optical fiber generating a spot diameter of less than 100 microns. The ablation was performed at a slower rotational velocity while the duodenal wall was stretched using a non-compliant balloon, such that the diameter of the ablated circles generated by the emitting optical fiber was approximately 20 mm, thus providing an ablative dose of 2 J/mm.

Figure 8:
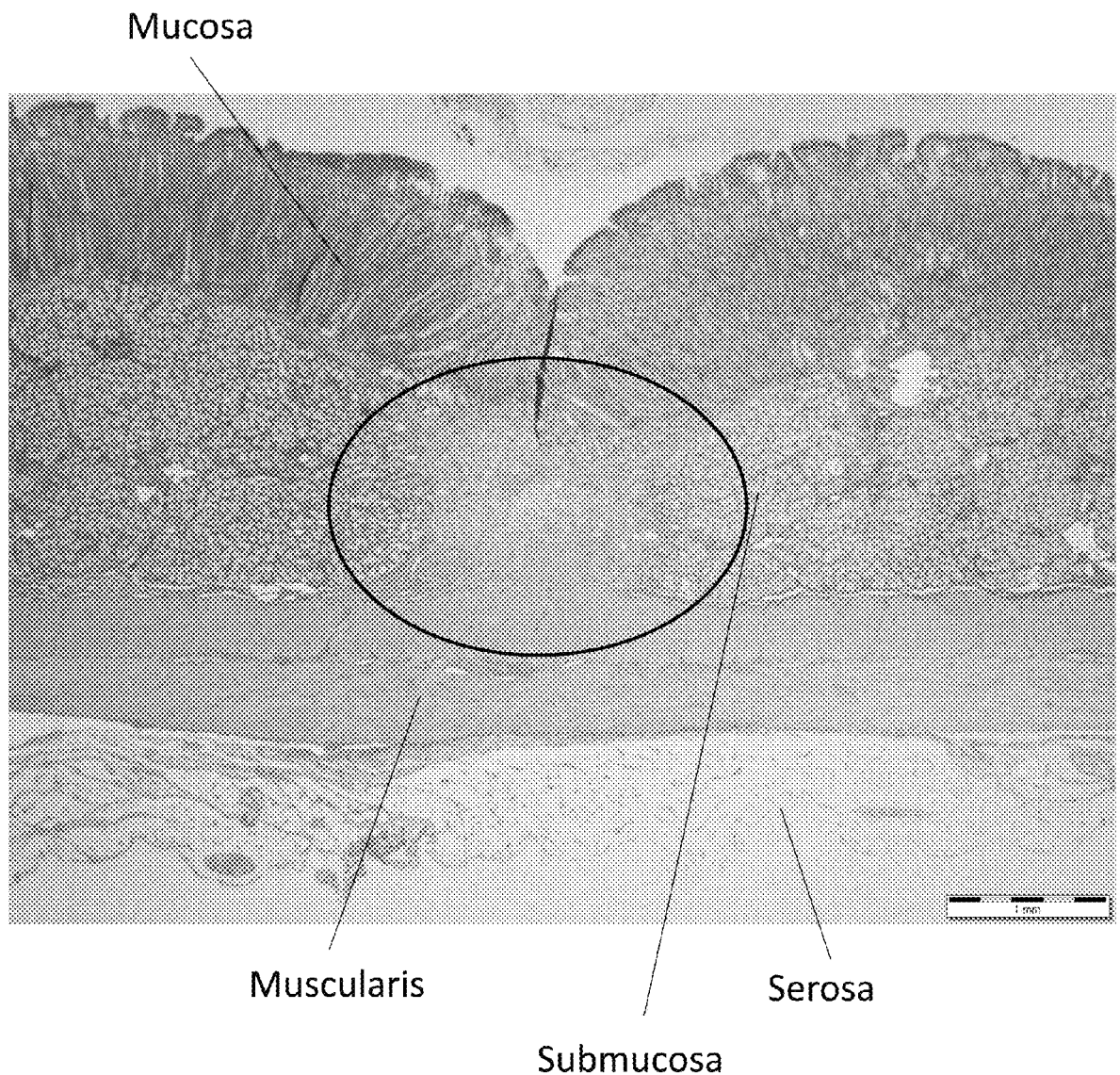
FIG. 8 shows a representative histological staining of duodenal tissue 2 weeks after a high dose ablative treatment using a single-mode optical fiber.

As seen from FIG. 8, which shows a representative histological staining of the treated duodenal tissue, 2 weeks after treatment, the higher ablative dose likewise caused a modification of the sub-mucosal tissue in an area (encircled) significantly larger than the initial point of impact, i.e. significantly larger than the spot diameter of less than 100 microns, along with changes in the shape of the duodenum wall as a result of an internal scar that typically leads to shrinkage of the duodenum. That is, a wide lateral modification of adjacent sub-mucosal tissue was observed (total area of impact ~1 mm$^2$). Advantageously, the scarring of the submucosal tissue indicates that the large ablative dose, provided to a relatively small area of impact, causes qualitative and/or structural changes to the submucosal tissue, which again advantageously reduces the ability of the sensory network to reestablish signaling, thus enhancing the sustainability of the treatment. Advantageously, despite the lateral spread of the impact, and despite the scaring of the sub-mucosal tissue no significant or irreversible damage was observed to the surrounding layers (mucosa, muscularis and serosa).

The examples described above are non-limiting examples and are not intended to limit the scope of the disclosure. The described examples may comprise different features, not all of which are required in all embodiments of the disclosure.

The invention claimed is:

1. A device for selectively ablating a submucosal layer of a duodenal wall and/or of sensory neurons therein, the device comprising a catheter comprising:
   a laser transmitting element comprising a single mode optical fiber coupled with the catheter body, said laser transmitting element, when in use, transmitting a laser beam having a wavelength of 1550 nm, a laser power in the range of 2-20 Watt, and a spot diameter below 200 microns;

a deflective optical element functionally coupled with the laser transmitting element and configured to direct the laser beam to the submucosal layer; and an expandable member configured to stretch the duodenal wall and to generate a fixed distance between the laser transmitting element and the duodenal wall, wherein the deflective element rotates the laser beam at a rotational velocity providing an ablative dose in the range of 0.5-2.5 J/mm to the submucosal layer;

thereby providing selective ablation of an area of the submucosal layer that is at least twice the size of the spot diameter, while essentially preventing damage of the surrounding mucosal, muscularis and/or serosal layers of the duodenal wall.

2. The device of claim 1, wherein the laser transmitting element has a core diameter of 8-10 microns.

3. The device of claim 1, wherein the single mode optical fiber is configured to transmit a laser beam having a spot diameter of 100 microns or less.

4. The device of claim 1, wherein the single mode optical fiber is configured to transmit a laser beam configured to selectively ablate an area of the submucosal layer that is at least three times the size of the spot diameter.

5. The device of claim 1, wherein the deflective element is configured to rotate the laser beam at a rotational velocity of about 2 mm/sec.

6. The device of claim 1, wherein the expandable member is configured to stretch the duodenal wall such that the fixed distance between the catheter's laser transmitting element and the duodenal wall is in the range of 15-30 mm.

7. The device of claim 6, wherein the expandable member is configured to stretch the duodenal wall, such that the fixed distance between the catheter's laser transmitting element and the duodenal wall is in the range of 20-25 mm.

8. The device of claim 1, wherein the expandable member is a non-compliant balloon.

9. The device of claim 1, wherein ablative dose of energy provided to the submucosal layer is in the range of 1-2 J/mm.

10. A method for selectively ablating a submucosal layer of a duodenal wall and/or of sensory neurons therein, the method comprising:
  inserting a catheter into a duodenum of a subject;
  deploying an expandable member delivered by the catheter, thereby stretching the duodenal wall and generating a fixed distance between the catheter's laser transmitting element and the duodenal wall;
  transmitting a laser beam in a direction essentially perpendicular to a longitudinal axis of the catheter, towards the duodenal wall, wherein the laser beam has a wavelength of 1550 nm, a laser power in the range of 2-20 Watt, and a spot diameter of less than 200 microns;
  rotating the laser beam at a rotational velocity providing an ablative dose in the range of 0.5-2.5 J/mm to the submucosal layer; thereby selectively ablating an area of the submucosal layer that is at least twice the size of the spot diameter while essentially preventing damage of the surrounding mucosal, muscularis and/or serosal layers of the duodenal wall.

11. The method of claim 10, wherein the laser beam has a spot diameter of 100 microns or less.

12. The method of claim 10, wherein the laser beam is configured to selectively ablate an area of the submucosal layer that is at least three times the size of the spot diameter.

13. The method of claim 10, wherein the laser beam is configured to be rotated at a rotational velocity of about 2 mm/sec.

14. The method of claim 10, wherein the fixed distance between the catheter's laser transmitting element and the duodenal wall is in the range of 15-30 mm.

15. The method of claim 14, wherein the fixed distance between the catheter's laser transmitting element and the duodenal wall is in the range of 20-25 mm.

16. The method of claim 10, wherein the ablative dose is determined by the distance between the catheter's laser transmitting element and the duodenal wall, the rotational velocity of the laser beam and the laser beam's power.

* * * * *